(12) United States Patent
Imura et al.

(10) Patent No.: US 6,713,420 B2
(45) Date of Patent: Mar. 30, 2004

(54) POROUS CERAMICS BODY FOR IN VIVO OR IN VITRO USE

(75) Inventors: Kohichi Imura, Hadano (JP); Takashi Umezawa, Hadano (JP); Akihiko Ichikawa, Hadano (JP); Katsuhiro Chaki, Hadano (JP)

(73) Assignees: Toshiba Ceramics Co., Ltd., Tokyo (JP); Independent Administrative Institution National Institute for Materials Science, Ibaraki (JP); Toshiba Denko Co., Ltd., Tokyo (JP)

( * ) Notice: Subject to any disclaimer, the term of this patent is extended or adjusted under 35 U.S.C. 154(b) by 176 days.

(21) Appl. No.: 09/973,079

(22) Filed: Oct. 10, 2001

(65) Prior Publication Data

US 2002/0052662 A1 May 2, 2002

(30) Foreign Application Priority Data

Oct. 13, 2000 (JP) ........................ 2000-312934
Feb. 9, 2001 (JP) ........................ 2001-033147
May 22, 2001 (JP) ........................ 2001-151934

(51) Int. Cl.$^7$ ............................................. C07B 25/35
(52) U.S. Cl. ..................... 501/80; 501/84; 501/123; 106/35; 623/16.11; 623/23.56; 623/23.61
(58) Field of Search ..................... 501/80, 123, 84; 106/35; 623/16.11, 23.56, 23.61

(56) References Cited

U.S. PATENT DOCUMENTS

| | | | |
|---|---|---|---|
| 4,654,314 A | | 3/1987 | Takagi et al. |
| 4,963,145 A | * | 10/1990 | Takagi et al. ................ 606/76 |
| 5,017,518 A | * | 5/1991 | Hirayama et al. ............. 501/1 |
| 5,650,108 A | | 7/1997 | Nies et al. |
| 6,340,648 B1 | * | 1/2002 | Imura et al. ................. 501/80 |

FOREIGN PATENT DOCUMENTS

| | | |
|---|---|---|
| EP | 0 253 506 | 1/1988 |
| EP | 0 369 034 A1 | 5/1990 |
| EP | 0 712 820 A1 | 5/1996 |
| GB | 2 078 696 A | 1/1982 |
| JP | 60-16879 | 1/1985 |
| JP | 60-40298 | 9/1985 |
| JP | 2-33388 | 7/1990 |
| JP | 5-33062 | 5/1993 |
| JP | 5-75427 | 10/1993 |
| JP | 5-305134 | 11/1993 |
| JP | 6-296676 | 10/1994 |
| JP | 7-291759 | 11/1995 |
| JP | 2576404 | 11/1996 |
| JP | 10-167853 | 6/1998 |
| JP | 2000-302567 | 10/2000 |
| WO | 93/04013 | 3/1993 |
| WO | 98/15505 | 4/1998 |
| WO | WO 98/38948 A1 | 9/1998 |

* cited by examiner

*Primary Examiner*—Paul Marcantoni
(74) *Attorney, Agent, or Firm*—Foley & Lardner

(57) ABSTRACT

A porous ceramics body for in vivo or in vitro 1use in which a number of pores are closely distributed in three dimensional directions, adjoining pores thereof being partitioned by wall portions with respective communication ports to bring said adjoining pores into communication with each other such that a series of connected spherical pores are formed therewithin, said porous ceramics body being made of a sintered calcium phosphate body, characterized in that, within said sintered calcium phosphate body, pores each having a diameter of 5 microns ($\mu$m) or more account for 80% or more of all the pores in terms of volume whereas pores having a diameter of less than 5 microns ($\mu$m) account for less than 20% of all the pores in terms of volume as subjected to a mercury porosimeter measurement.

7 Claims, 20 Drawing Sheets

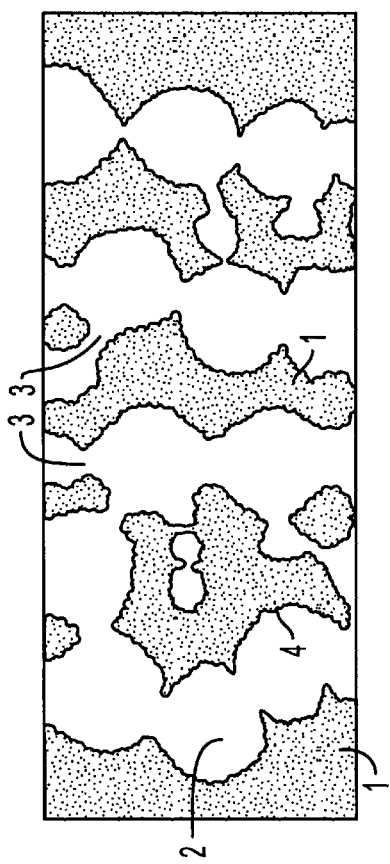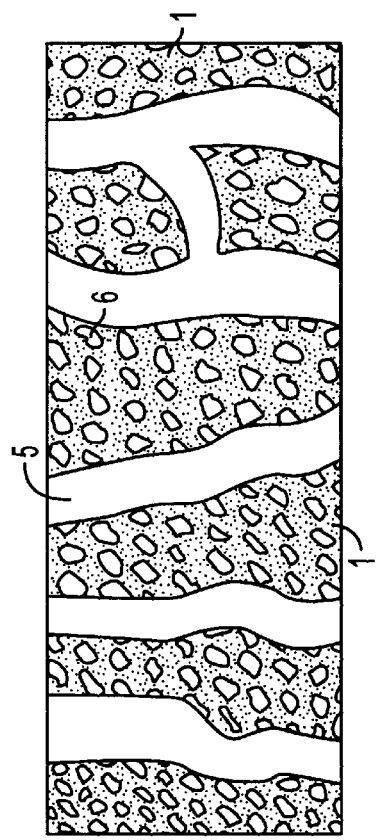
FIG. 1
FIG. 2

POROUS CERAMICS BODY FOR IN VIVO OR IN VITRO USE

BACKGROUND OF THE INVENTION

1. Field of the Invention

The present invention relates to a porous ceramics body for in vivo and in vitro use and more particularly to a porous ceramics body for in vivo use made of a calcium phosphate sintered material which is preferably used for artificial bones and as a filling material for such artificial bones and has an excellent property in forming osseous tissues of a living body as well as a high degree of strength and also to a culture vessel for cells.

2. Description of the Related Art

In the medical fields such as surgery or orthopaedic surgery, the reconstruction of osseous tissues of a patient having defective portions or cavities in his or her bones caused by a disease, an accident or an surgical operation was conventionally practiced by collecting osseous materials from another portion of the patient's own body or the body of his or her parent, relatives, brothers or sisters to fill such defective portions or cavities.

However, a surgical operation for collecting such osseous materials is accompanied by unbearable pains in addition to requiring tremendous expenses and labor. Further, there is a limitation in filling the defective portions with human osseous materials alone and, if the defective portions in the patient's body covers an extensive area, it is very often impossible to secure a sufficient amount of human osseous materials.

Recently, therefore, the research work on artificial filling material for bones came to be strenuously conducted.

In this connection, it is needed in burying artificial osseous materials that such artificial osseous materials are nontoxic and safe as well as having a high degree of mechanical strength and affinity with living tissues such that said artificial osseous materials easily become integrated with osseous tissue cells and vessel systems. Such material so far proposed includes sintered calcium phosphates such as tricalcium phosphate, hydroxy apatite or the like.

However, there is a problem that osseous tissues in a living body are not formed quickly if a sintered nonporous (or solid) member of calcium phosphate is buried therein with the result that an extremely long time is needed for recovery.

Therefore, it is proposed to provide a sintered porous body of calcium phosphate which is to be buried in a living body to assure a quick integration with a living tissues after actually buried; that is, there is proposed a sintered porous body of calcium phosphate which allows easy entry of osseous tissues.

The thus proposed conventional sintered porous body of calcium phosphate is formed of immature sintered porous material having an innumerable number of fine open pores in the walls portions. Here, the reference to the immature sintered porous body was made to clarify that the crystalline particles to form a sintered body are not sufficiently connected, thus leaving gaps therebetween with the result that a number of fine pores having diameters substantially smaller than those of the crystalline particles are dispersed all over the sintered body.

With the immature sintered porous body having an innumerable number of fine pores in the walls portions (the diameters of the majority of said pores are as small as the order of microns ($\mu$m) or less), it was conventionally thought that formation of bones are actively done by virtue of such fine pores.

Now back to the proposed conventional porous ceramics body for in vivo use (sintered porous body of calcium phosphate), there is a problem that said body cannot be used for treatment of large defective portions in a bone because sufficient mechanical strength as required for an artificial bone is not attained as the immature sintered porous body has an innumerable number of fine open pores in the wall portions.

On the other hand, there is another problem that an extremely long period of time is needed for recovery of the patient because osseous tissues in a living body are not quickly formed if a solid sintered body of calcium phosphate is used for the ceramics body for in vivo use in order to assure the mechanical strength as mentioned above.

The inventors made an intensive research work in order to overcome the above shortcomings of the conventional porous ceramics body for in vivo use (a sintered body of calcium phosphate). As a result, the reduction of strength in the sintered body of calcium phosphate was found less if said ceramics body of calcium phosphate has a particular pore structure, thus retaining the strength required for artificial bones and artificial osseous filling material. Further, it was found that said particular pore structure of the sintered calcium phosphate body assures quick formation of osseous tissues as a result of osseous tissue cells (osteoblast cells) and blood vessels entering the pores such that formation of the osseous tissues is prompted. Based on this knowledge, the inventors have completed the porous ceramics body for in vivo or in vitro use according to the present invention.

SUMMARY OF THE INVENTION

The present invention has been made to solve the problems discussed hereinbefore and its object is to provide a porous ceramics body for in vivo or in vitro use which is excellent in maintaining a sufficient mechanical strength while prompting the formation of osseous system tissues such that suitable artificial bones, an artificial filling material for osseous systems.

The porous ceramics body according to the present invention is characterized in that a number of pores are closely distributed in three dimensional directions, adjoining pores thereof being partitioned by wall portions formed with respective communication ports to bring said adjoining pores into communication with each other such that a vacancy of a series of spherical pores are formed therewithin, said porous ceramics body being made of a sintered calcium phosphate body, characterized in that, within said sintered calcium phosphate body, pores each having a diameter of 5 microns ($\mu$m) or more account for 80% or more of all the pores in terms of volume whereas pores having a diameter of less than 5 microns ($\mu$m) account for less than 20% of all the pores in terms of volume as subjected to a mercury porosimeter measurement.

As disclosed hereinbefore, the porous ceramics body according to the present invention is characterized in that a series of spherical pores are closely distributed in three dimensional directions such that said series of spherical pores allow the entry of osseous system cells (osteoblast cells) thereinto through the communication ports whereas adjoining pores are partitioned by wall portions in which there are substantially no open pores having a diameter of less than 5 microns ($\mu$m), said porous ceramics body being made of a sintered calcium phosphate body.

That is, the porous ceramics body for in vivo use according to the present invention is made of the sintered calcium phosphate body of the aforementioned structure having therein a number of open pores to allow the entry of osseous system cells (osteoblast cells or the like) and blood vessels thereinto whereas there are substantially no pores except the communication ports in the wall portions.

Further, it is preferable that the volume of the pores having a diameter of 5 microns ($\mu$m) or more accounts for 90% of all the pores or more and the ratio of 93% or more is further preferable.

Therefore, it is easy for osseous system cells (osteoblast cells or the like) to enter the porous body, thus prompting the formation of osseous systems. Further, the substantial absence of pores in the wall portions prevents remarkable reduction in the mechanical strength as compared with a solid sintered calcium phosphate body with the result that a predetermined mechanical strength required for artificial bones is assured.

In this connection, it is to be noted that it is achieved by complete sintering to minimize fine pores in the wall portions which partition adjoining pores like in the porous ceramics body according to the present invention. The complete sintering means in this context that crystalline particles constituting the sintered body are completely connected to each other leaving no gaps therebetween to such an extent that there are substantially no pores smaller than the crystalline particles all through the sintered body.

Further, it was observed that osseous systems are sufficiently formed in the completely sintered body like in the porous ceramics body according to the present invention and that the porous ceramics body according to the present invention is suitable for artificial bones and a filling material for artificial osseous systems.

It is preferable here that pores accounting for an accumulated ratio of 50% in terms of volume have a diameter of 10 to 600 microns ($\mu$m) as subjected to a mercury porosimeter measurement.

In this way, since pores accounting for an accumulated ratio of 50% in terms of volume have a diameter in the range of 10 to 600 microns ($\mu$m) as subjected to a mercury porosimeter measurement, osseous system cells (osteoblast cells or the like) are quickly admitted into the porous ceramics body for in vivo or in vitro use to prompt the formation of osseous systems.

It is to be noted that it is impossible to effectively admit osseous system cells (osteoblast cells or the like) into the porous ceramics body for in vivo or in vitro use if pores accounting for an accumulated ratio of 50% in terms of volume have a diameter less than 10 microns ($\mu$m). If, on the other hand, pores accounting for an accumulated ratio of 50% in terms of volume have a diameter more than 600 microns ($\mu$m), osseous system cells (osteoblast cells or the like) which have been admitted thereinto will flow out without making the formation of osseous systems. Therefore, it is preferable that pores accounting for an accumulated ratio of 50% in terms of volume have a diameter of 10 to 600 microns ($\mu$m) as subjected to a mercury porosimeter measurement.

It is further preferable that pores accounting for an accumulated ration of 50% in terms of volume have a diameter of 20 to 200 microns ($\mu$m) if the mechanical strength thereof and the cell entry and subsequent stability thereat is to be considered and, in this respect, the diameter of 30 to 100 microns ($\mu$m) is still further preferable.

It is still further preferable that said sintered calcium phosphate body has a porosity of 45 to 90%.

If the porosity is less than 45%, the distribution of the pores is too sparse to obtain a series of spherical pores in mutual communication. A porous ceramics body which does not have a series of spherical pores in mutual communication has a problem that osseous system cells (osteoblast cells or the like) will not be admitted thereinto.

Further, if the porosity of the sintered calcium phosphate body is more than 90%, the mechanical strength of the porous ceramics body falls to such an extent the same is not suitable for artificial bones.

Therefore, it is preferable that said sintered calcium phosphate body has a porosity of 45 to 90%.

It is further preferable that said sintered calcium phosphate body is a sintered body made of a material selected from hydroxy apatite, tricalcium phosphate and a composite material thereof. Hydroxy apatite is particularly preferable.

Such sintered calcium phosphate body adopted for the porous ceramics body for in vivo use has an affinity with the human body and converted into complete osseous systems. Therefore, the need for a re-operation to remove surgical titanium or stainless steel members is eliminated.

It is further preferable that each wall portion has a surface spread with calcium phosphate particles closely as if stone pavement, given calcium phosphate particles cooperating to define a recess therebetween, said recess having a diameter equal to or less than a mean particle diameter.

Due to the structure as disclosed above, cells take root uniformly and extensively. Further, the particles hardly fall off from the surface of the wall portions of the porous ceramics body such that there is no cause for cracks to be formed, thus improving the strength thereof. Further, calcium phosphate particles are securely joined to each other to prevent them from falling off therefrom such that washing thereof is easily done.

In this connection, the disclosure to the effect that given calcium phosphate particles cooperate to define a recess therebetween and that said recess has diameter equal to or less than a mean particle diameter means that the height h shown in FIG. 15 is equal to or less than a mean particle diameter. Such calcium phosphate particles and those therearound make a flat surface, thus providing an extensive contact area between the particles which prevents a possibility to drop therefrom and contributes to improvement of strength. If there is cutting dust on the surface, it can be difficult for fluid to enter the sintered calcium phosphate body. The sintered calcium phosphate body according to the present invention controls generation of floating particles like the cutting dust as mentioned above. Therefore, the risk of floating particles preventing the entry of the fluid thereinto is eliminated.

In addition, as well known by a person skilled in art, a diameter of the pores as subjected to a mercury porosimeter measurement is being defined as the narrowest part within the series of open pores and corresponds with communication ports 3 in FIG. 1.

BRIEF DESCRIPTION OF THE DRAWINGS

FIG. 1 is an explanatory cross-sectional view of a porous structure in the sintered body of calcium phosphate forming a porous ceramics body for in vivo use according to the present invention;

FIG. 2 is an explanatory cross-sectional view of a typical porous structure in the prior art sintered body of calcium phosphate;

DESCRIPTION OF THE PREFERRED EMBODIMENTS

Figure 3A:
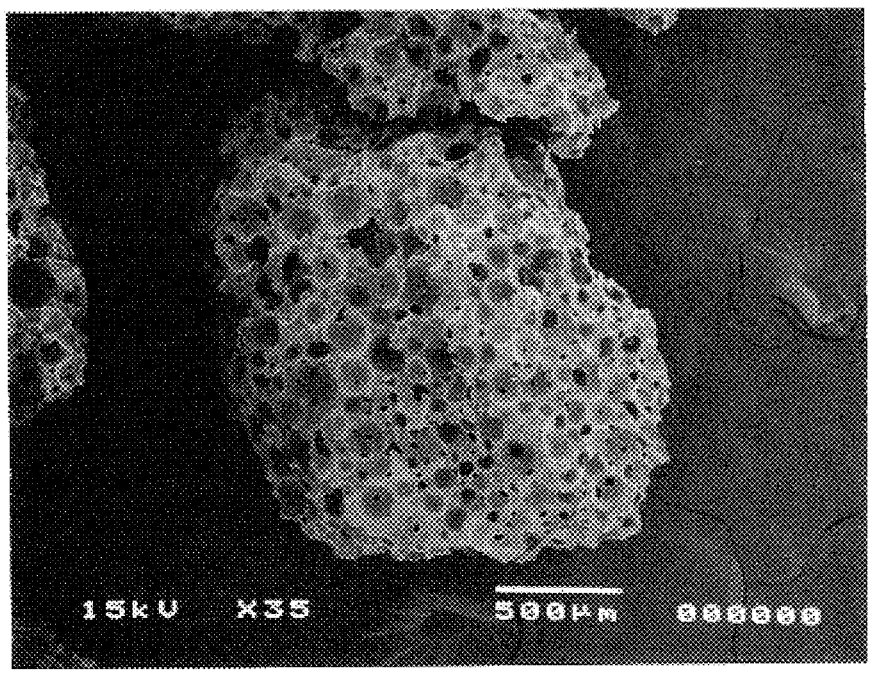
FIGS. 3a through 3c show electron microscopic pictures of porous ceramic body made of hydroxy apatite to be explained in the embodiment of the present invention (magnification of 35 in FIG. 3a, magnification of 150 in FIG. 3b, and magnification of 10,000 in FIG. 3c)

Hereinafter, one embodiment of the present invention directed to a porous ceramics member for in vivo or in vitro use will be explained specifically and in detail with reference to the attached drawings. In this connection, the embodiment of the present invention and the prior art will be compared to explain the invention such that the porous ceramics member for in vivo use in accordance with the present invention will be more easily understood.

First of all, the porous structure of the embodiment in accordance with the present invention will be explained referring to FIG. 1 whereas the prior art structure will be explained referring to FIG. 2. It is to be noted in this connection that FIG. 1 is an explanatory cross-sectional view of the porous structure in the sintered body of calcium phosphate forming a porous ceramics body for in vivo or in vitro use according to the present invention whereas FIG. 2 is an explanatory cross-sectional view of the typical porous structure in the sintered body of calcium phosphate in the prior art.

The embodiment of the invention shown in FIG. 1 explains a porous ceramics body made of a sintered calcium phosphate material, in which a number of pores 2 are closely distributed in three dimensional directions, adjoining pores thereof being partitioned by wall portions 1 which form respective communication ports 3 among the pores 2. And in the form of a series of spherical pores 2 is formed. Said wall portions per se which partition said series of spherical pores have substantially no pores formed therein. Further, the surfaces of the wall portions 1 are formed with irregularities in the form of fine recesses.

By contrast, the prior art porous ceramics body for in vivo use as shown in FIG. 2 has a porous structure within in which there are formed a number of pores 5 extending in three dimensional directions. Further, there are wall portions 1 to partition the pores 5, said wall portions per se being formed with fine pores 6 therewithin.

In this way, the porous ceramics body for in vivo use according to the present invention is formed with the spherical pores 2 in communication with each other to be densely distributed therewithin in three dimensional directions so as to allow easy entry of osseous tissue cells (osteoblast cells) or capillary vessel cells thereinto, thus prompting formation of osseous systems.

Particularly, since the wall portions 1 to partition adjoining spherical pores 2 in the present invention have no fine pores 6 as found in the prior art, there is no remarkable reduction in mechanical strength thereof.

Next, the porous structure in the embodiment of the present invention and the prior art porous structure will be shown referring to FIGS. 3 through 8.

Figure 3B:
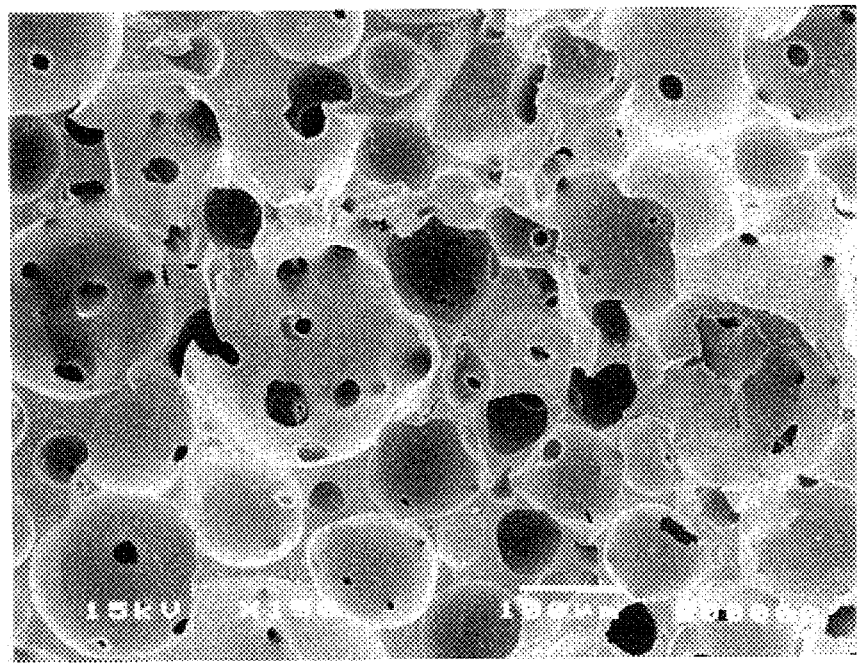
Figure 3C:
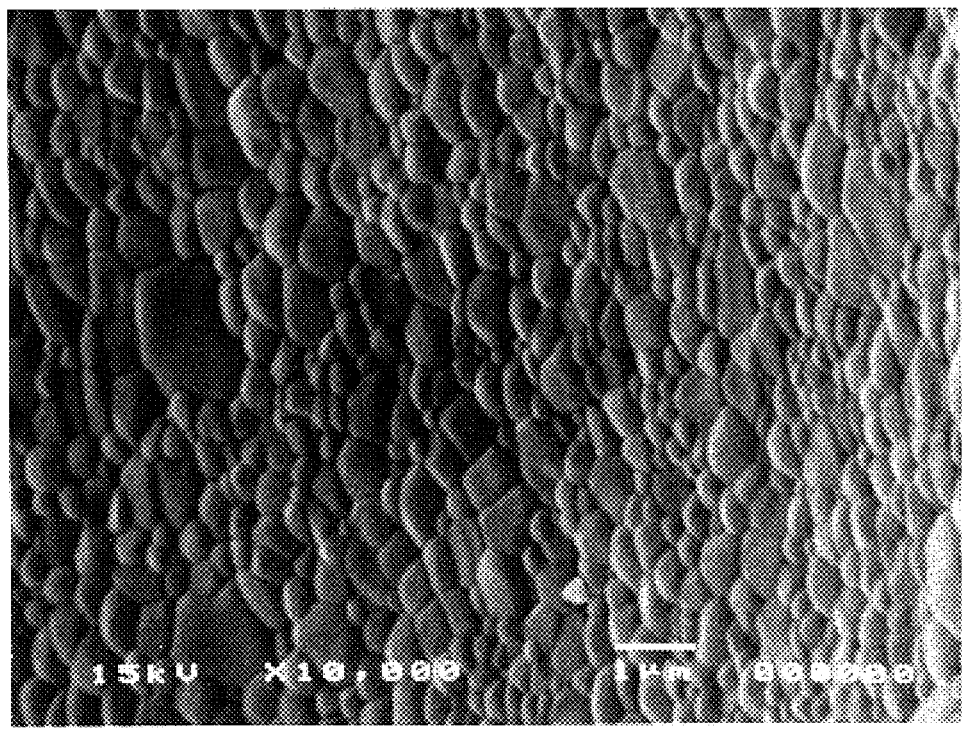

FIGS. 3a, 3b and 3c are electron microscopic pictures of porous ceramics body according to the present invention in which said body is made of hydroxy apatite; FIG. 3a picture was taken by an electron microscope with a magnification power of 35, FIG. 3b picture was taken by an electron microscope with a magnification power of 150, and FIG. 3c picture was taken by an electron microscope with a magnification power of 10,000.

Figure 4A:
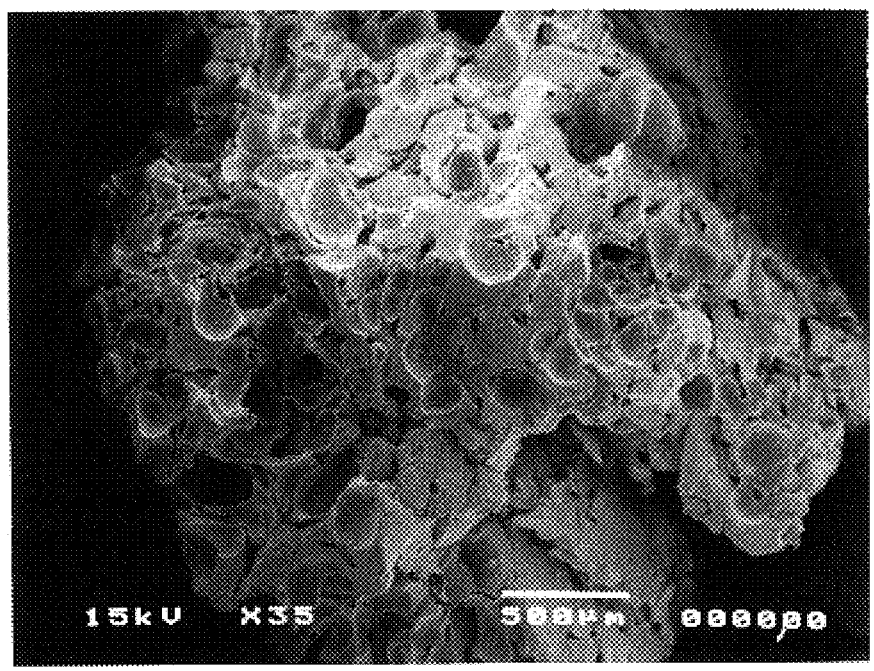
FIGS. 4a through 4c show electron microscopic pictures of a prior art porous ceramic body for in vivo use (magnification of 35 in FIG. 4a, magnification of 150 in FIG. 4b, and magnification of 10,000 in FIG. 4c)
Figure 4B:
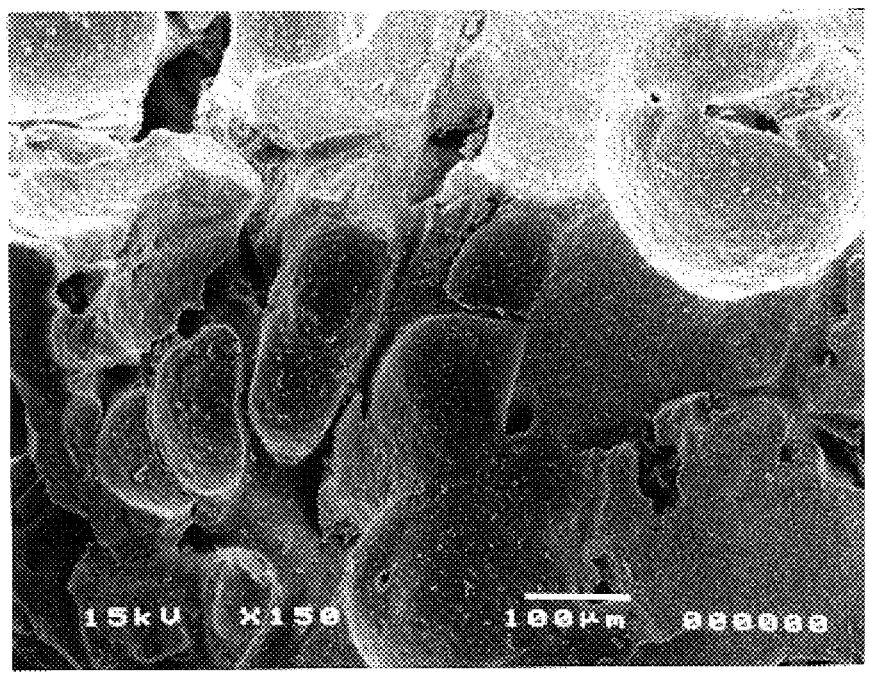
Figure 4C:
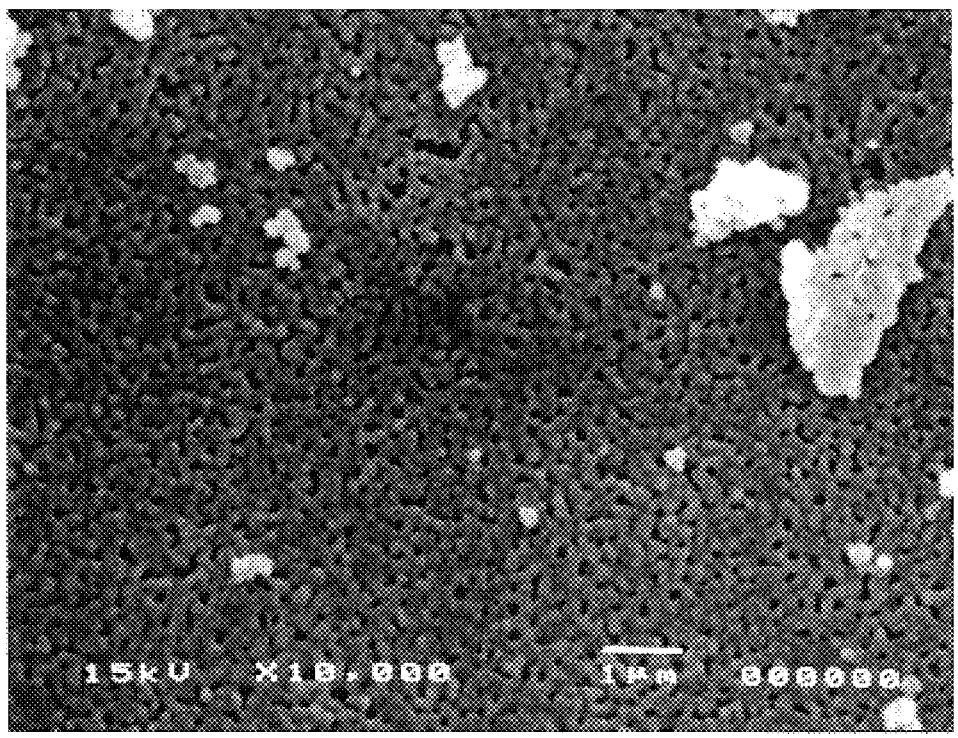

FIGS. 4a, 4b and 4c are electron microscopic pictures of a prior art porous ceramics body for in vivo use (manufactured by company A); FIG. 4a picture was taken by an electron microscope with a magnification power of 35, FIG. 4b picture was taken by an electron microscope with a magnification power of 150, and FIG. 4c picture was taken by an electron microscope with a magnification power of 10,000.

Figure 5A:
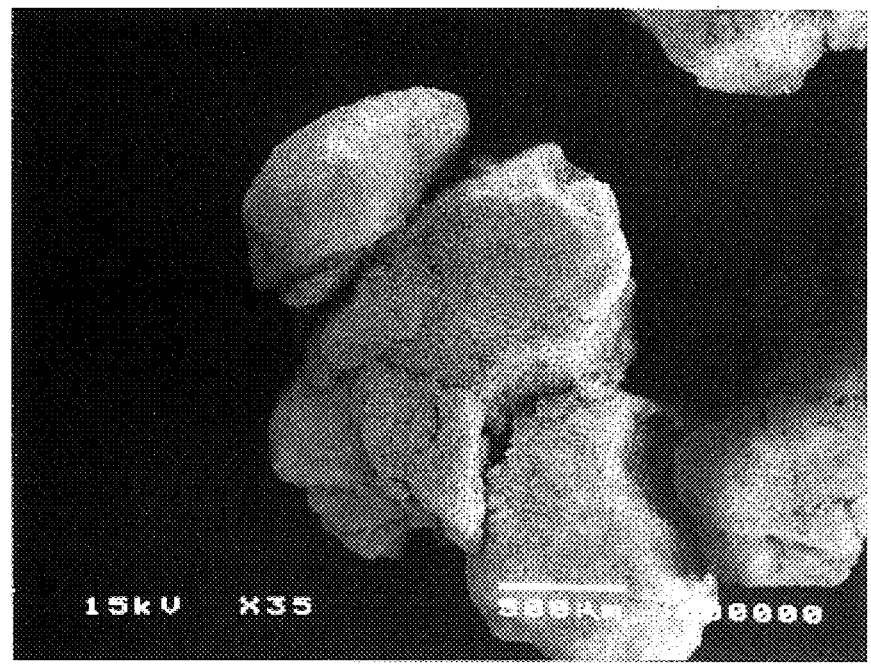
FIGS. 5a through 5c show electron microscopic pictures of another prior art porous ceramic body for in vivo use (magnification of 35 in FIG. 5a, magnification of 150 in FIG. 5b, and magnification of 10,000 in FIG. 5c)
Figure 5B:
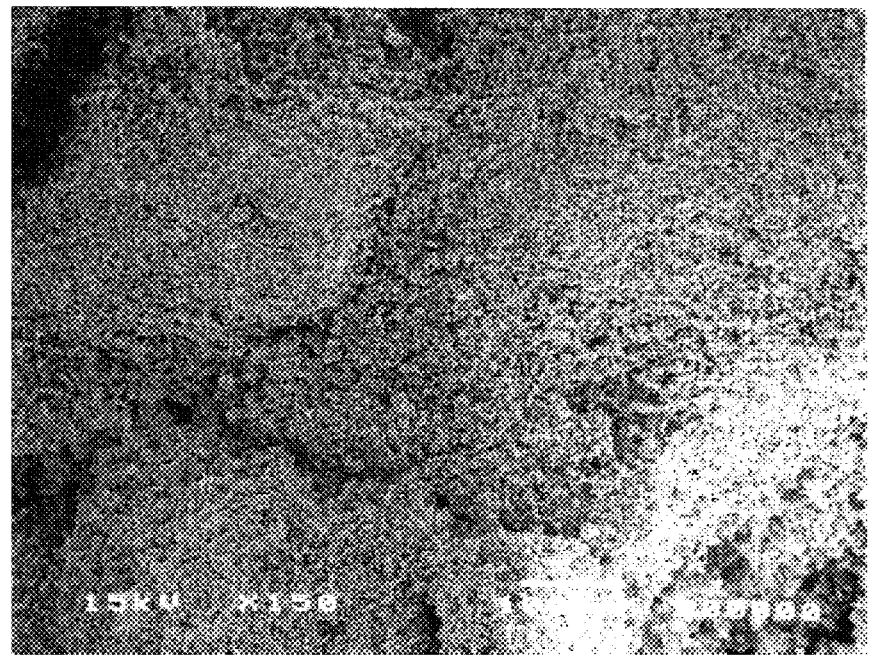
Figure 5C:
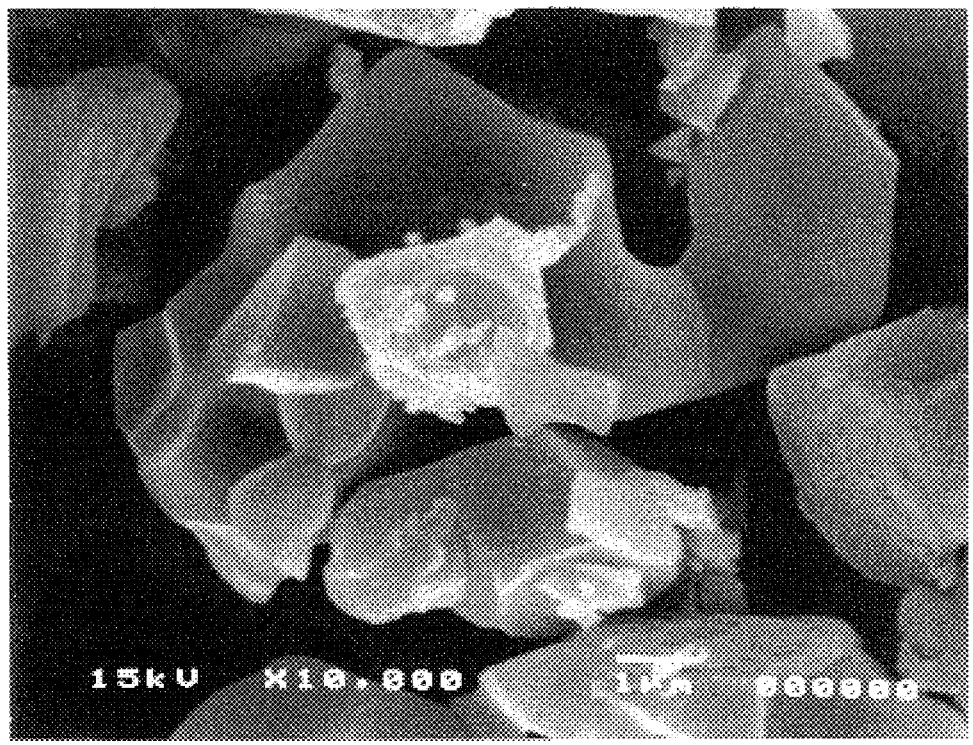

FIG. 5a, FIG. 5b and FIG. 5c are electron microscopic pictures of another prior art porous ceramics body for in vivo use (manufactured by company B); FIG. 5a picture was taken by an electron microscope with a magnification power of 35, FIG. 5b picture was taken by an electron microscope with a magnification power of 150, and FIG. 5c picture was taken by an electron microscope with a magnification power of 10,000.

Figure 6A:
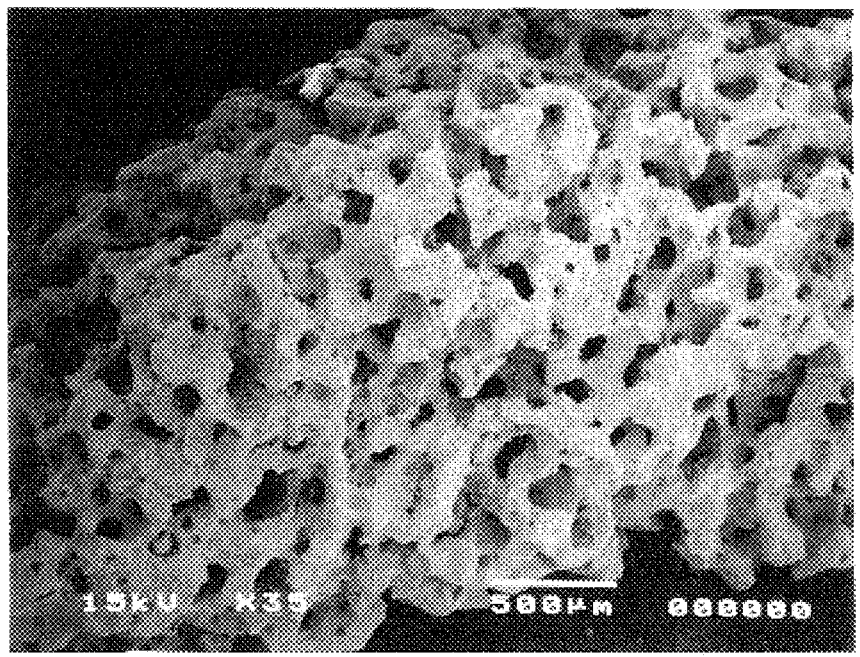
FIGS. 6a through 6c show electron microscopic pictures of a further prior art porous ceramic body for in vivo use (magnification of 35 in FIG. 6a, magnification of 150 in FIG. 6b, and magnification of 10,000 in FIG. 6c)
Figure 6B:
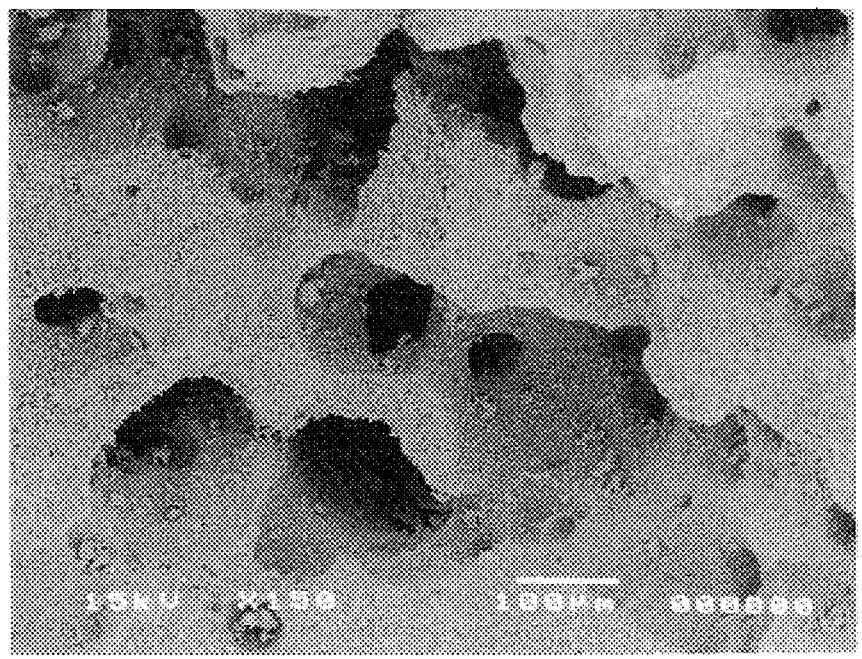
Figure 6C:
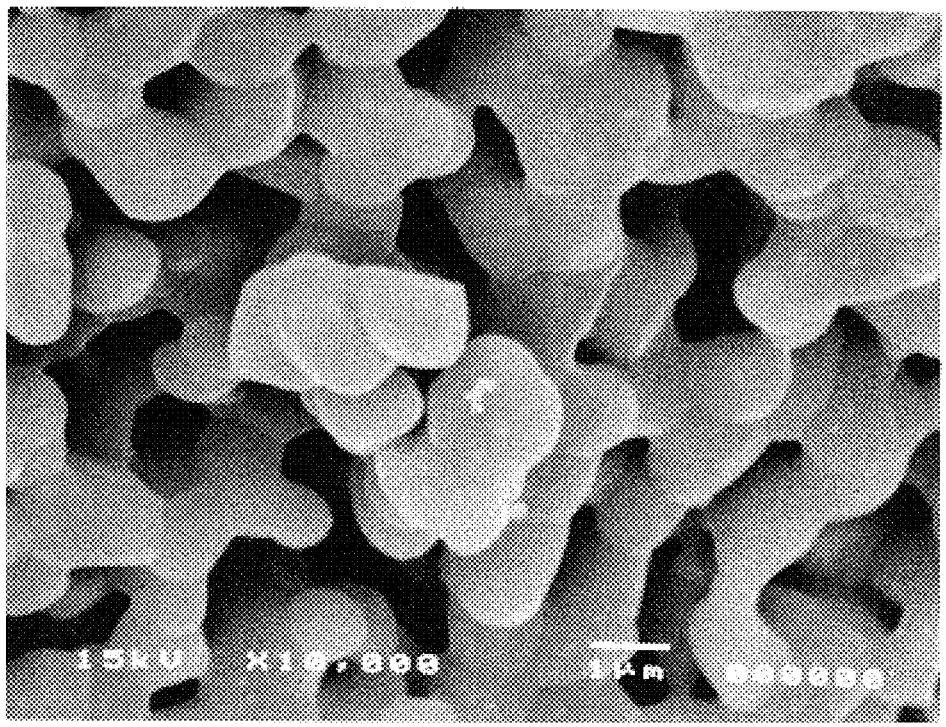

FIG. 6a, FIG. 6b and FIG. 6c are electron microscopic pictures of a further prior art porous ceramics body for in vivo use (manufactured by company C); FIG. 6a picture was taken by an electron microscope with a magnification power of 35, FIG. 6b picture was taken by an electron microscope with a magnification power of 150, and FIG. 6c picture was taken by an electron microscope with a magnification power of 10,000.

Figure 7A:
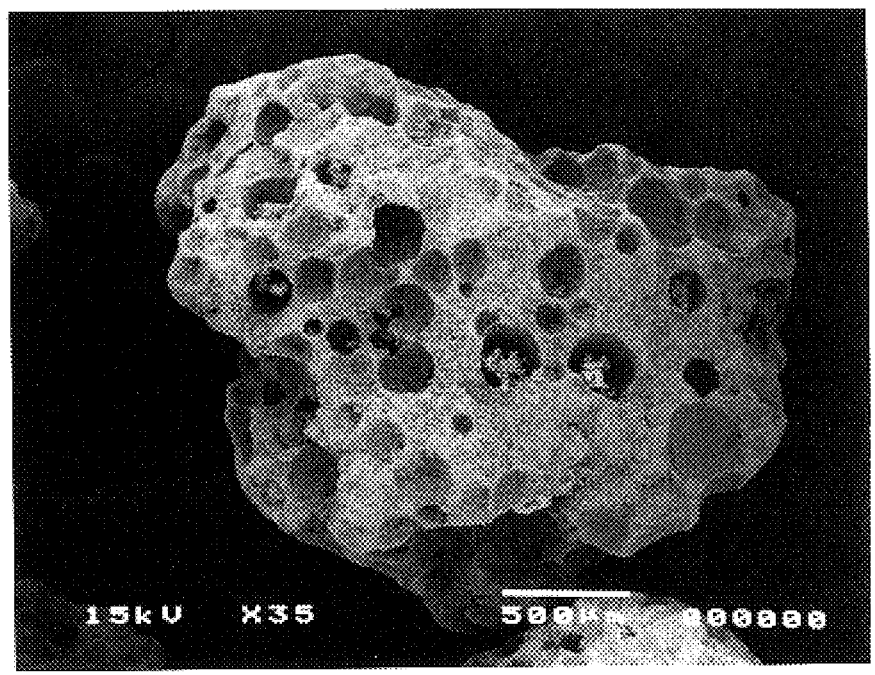
FIGS. 7a through 7c show electron microscopic pictures of a still further prior art porous ceramic body for in vivo use (magnification of 35 in FIG. 7a, magnification of 150 in FIG. 7b, and magnification of 10,000 in FIG. 7c)
Figure 7B:
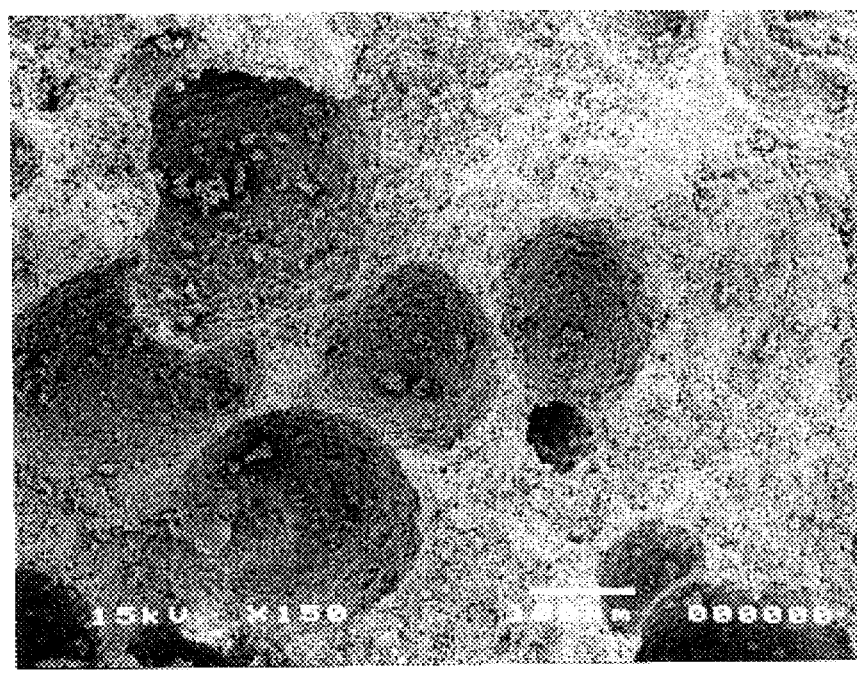
Figure 7C:
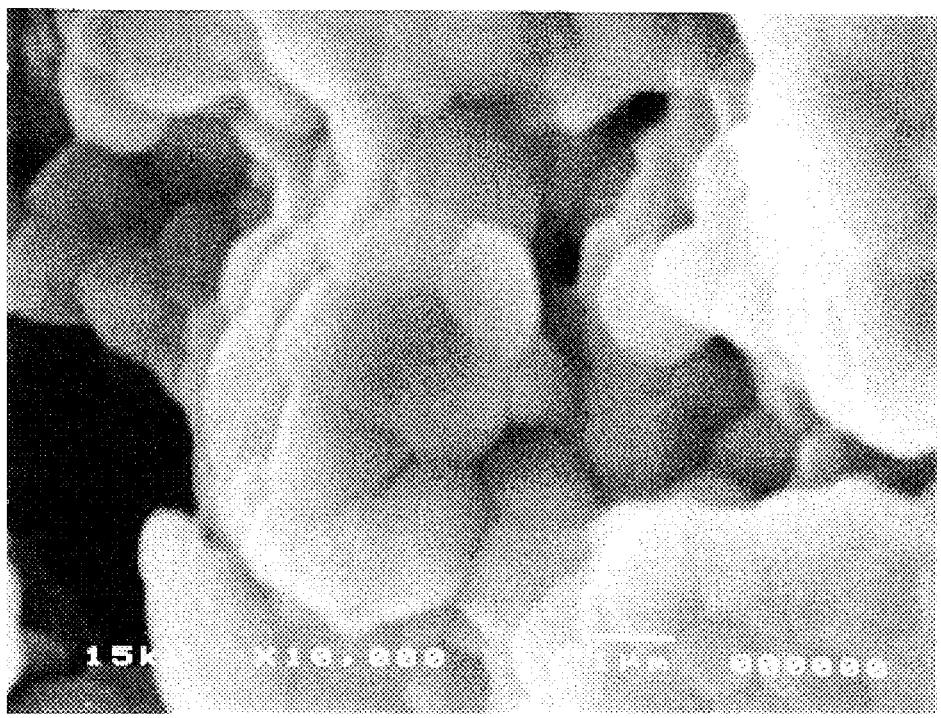

FIG. 7a, FIG. 7b and FIG. 7c are electron microscopic pictures of a still further prior art porous ceramics body for in vivo use (manufactured by company D); FIG. 7a picture was taken by an electron microscope with a magnification power of 35, FIG. 7b picture was taken by an electron microscope with a magnification power of 150, and FIG. 7c picture was taken by an electron microscope with a magnification power of 10,000.

Figure 8A:
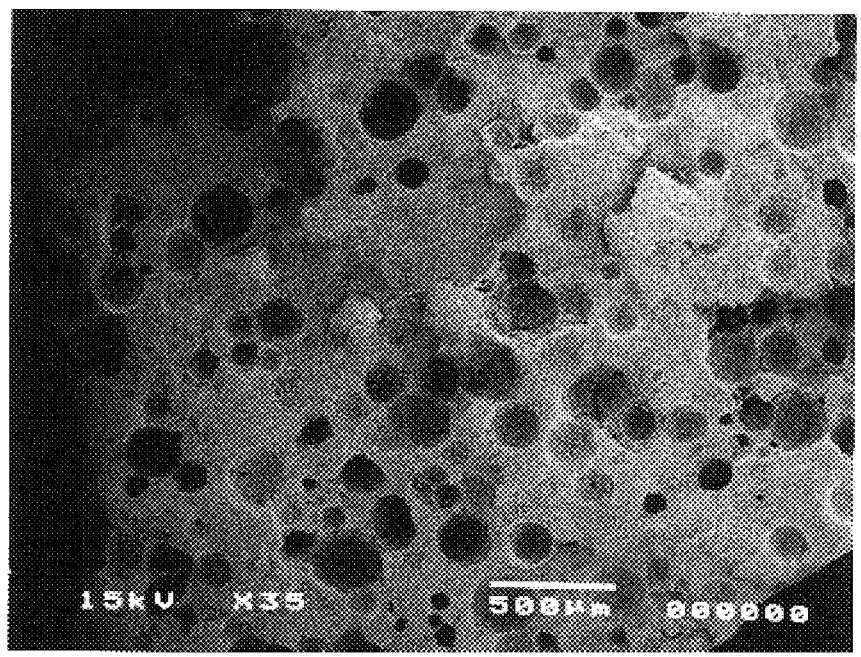
FIGS. 8a through 8c show electron microscopic pictures of a still further prior art porous ceramic body for in vivo use (magnification of 35 in FIG. 8a, magnification of 150 in FIG. 8b, and magnification of 10,000 in FIG. 8c)
Figure 8B:
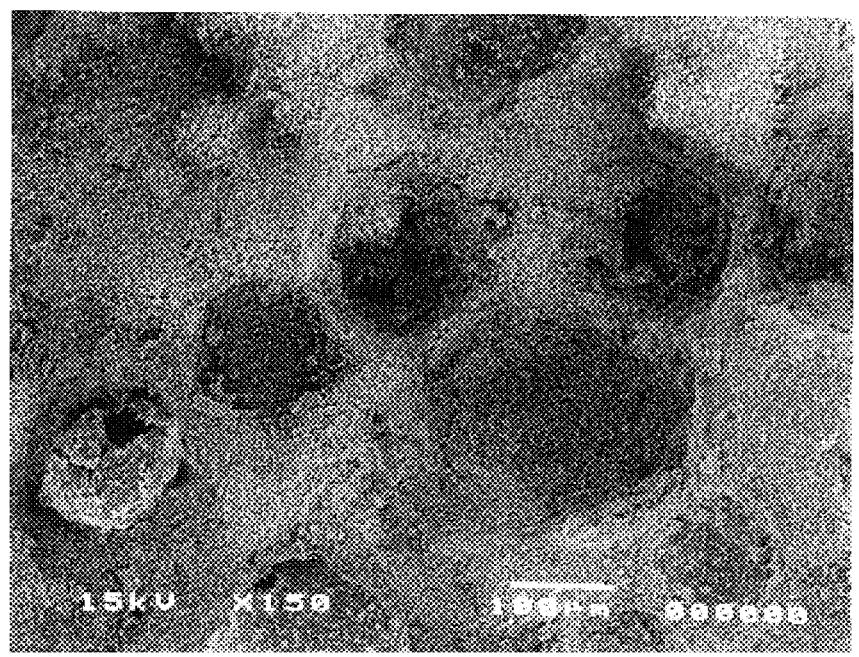
Figure 8C:
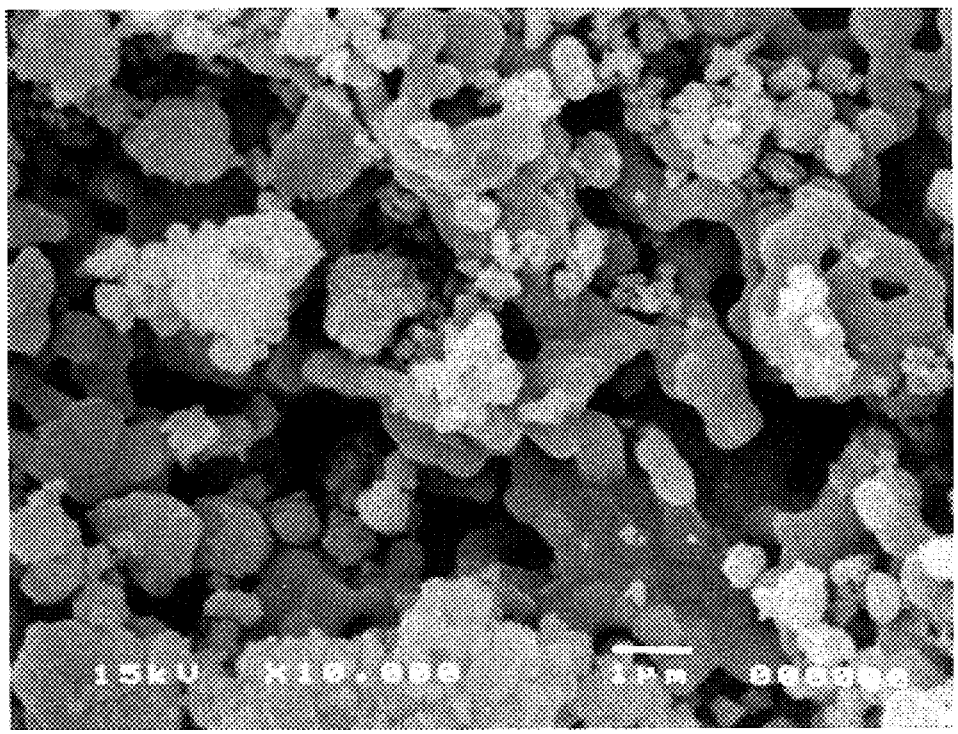

FIG. 8a, FIG. 8b and FIG. 8c are electron microscopic pictures of a still further prior art porous ceramics body for in vivo use (manufactured by company E); FIG. 8a picture was taken by an electron microscope with a magnification power of 35, FIG. 8b picture was taken by an electron microscope with a magnification power of 150, and FIG. 8c picture was taken by an electron microscope with a magnification power of 10,000.

As clearly seen from the above electron microscopic pictures in the present invention, the majority of the wall portions 1 of the porous ceramics body has no fine pores but is formed with fine irregularities in the form of recesses in the surface thereof. By contrast, the wall portions 1 of the prior art porous ceramics body are formed with fine pores 6 therewithin and the communication ports are not formed.

Next, the distribution of the fine pores in the porous ceramics body according to the present invention and the prior art counterpart are subjected to a mercury porosimeter examination (press charged mercury method). The result thereof will be shown in FIGS. 9 through 14.

Figure 9:
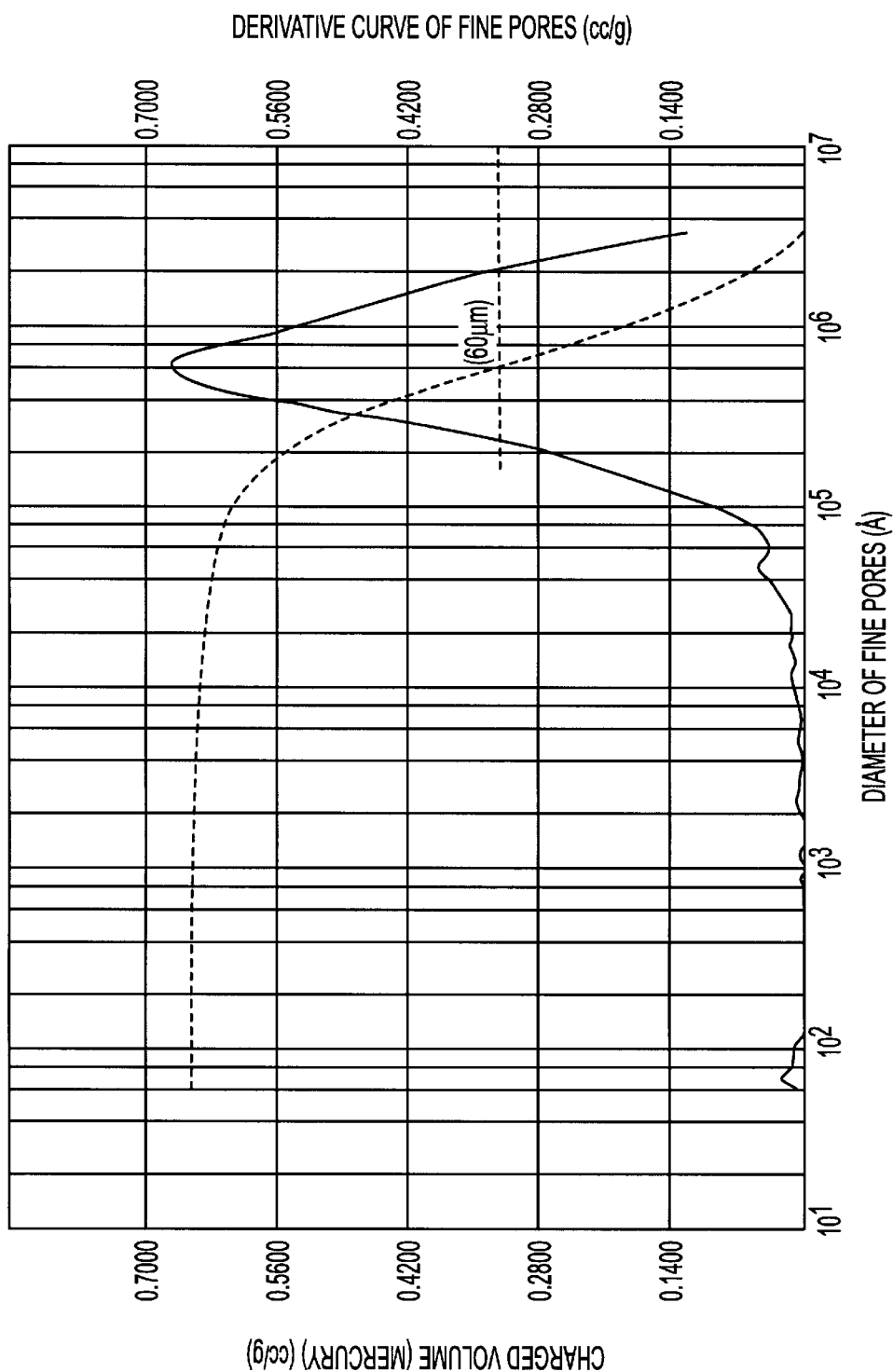
FIG. 9 is a graph showing a dispersion of fine pores in the porous ceramics body (a specimen of FIG. 2) in accordance with the present invention as plotted by a press charged mercury method.
Figure 10:
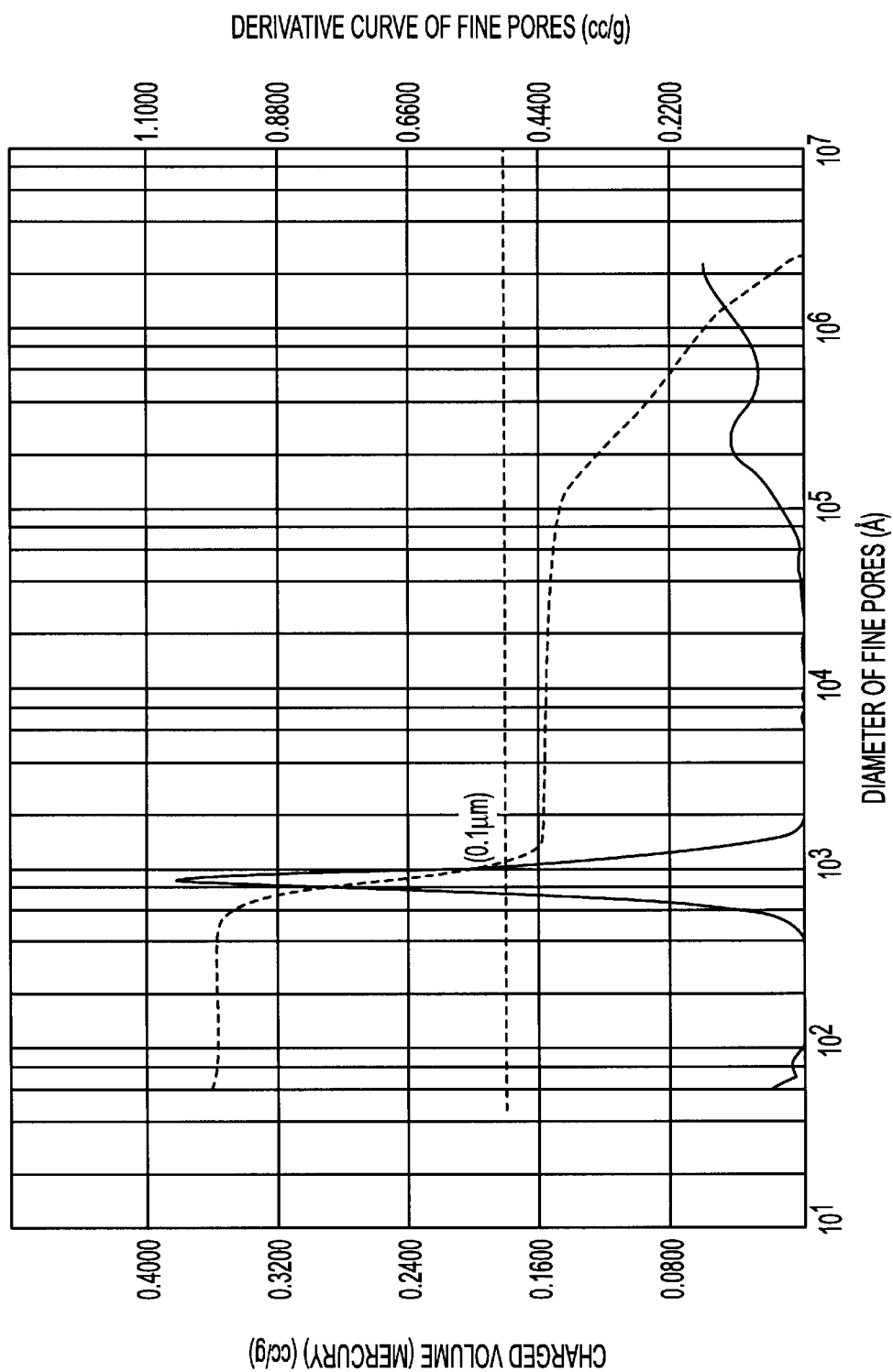
FIG. 10 is a graph showing a dispersion of fine pores in the prior art body (a specimen of FIG. 4 as plotted by a press charged mercury method)
Figure 11:
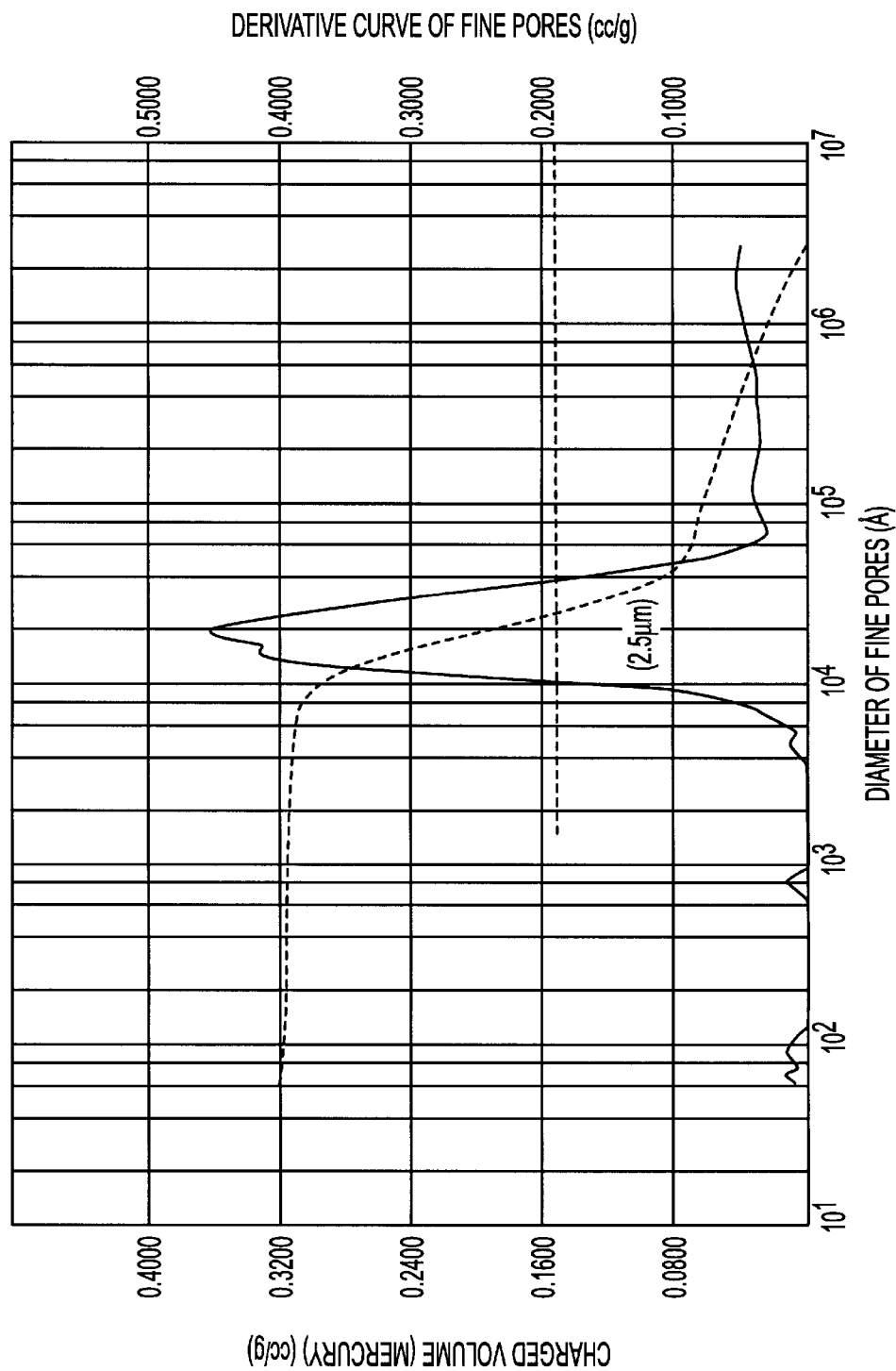
FIG. 11 is a graph showing a dispersion of fine pores in the prior art body (a specimen of FIG. 5 as plotted by a press charged mercury method)
Figure 12:
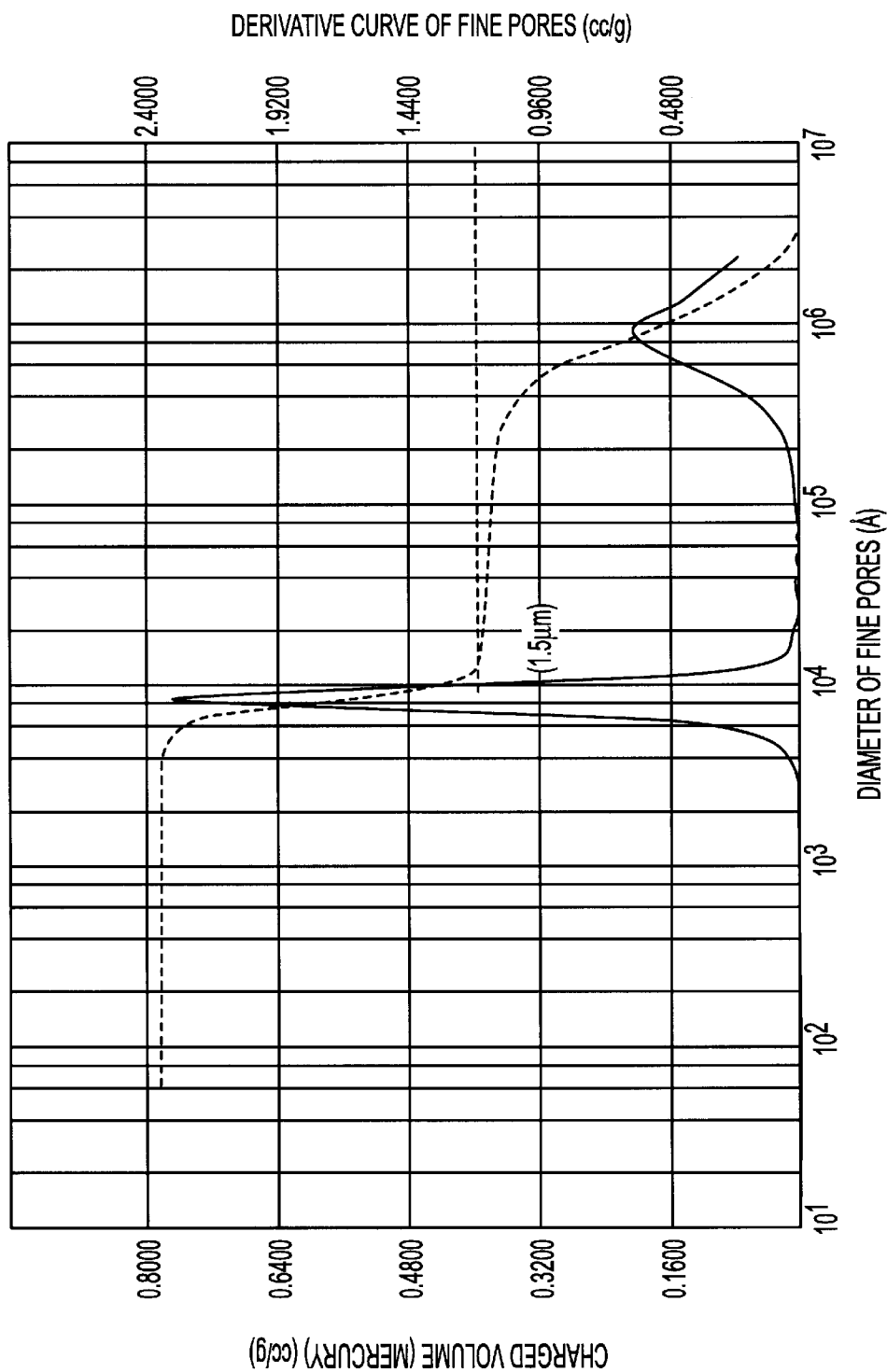
FIG. 12 is a graph showing a dispersion of fine pores in the prior art body (a specimen of FIG. 6 as plotted by a press charged mercury method)
Figure 13:
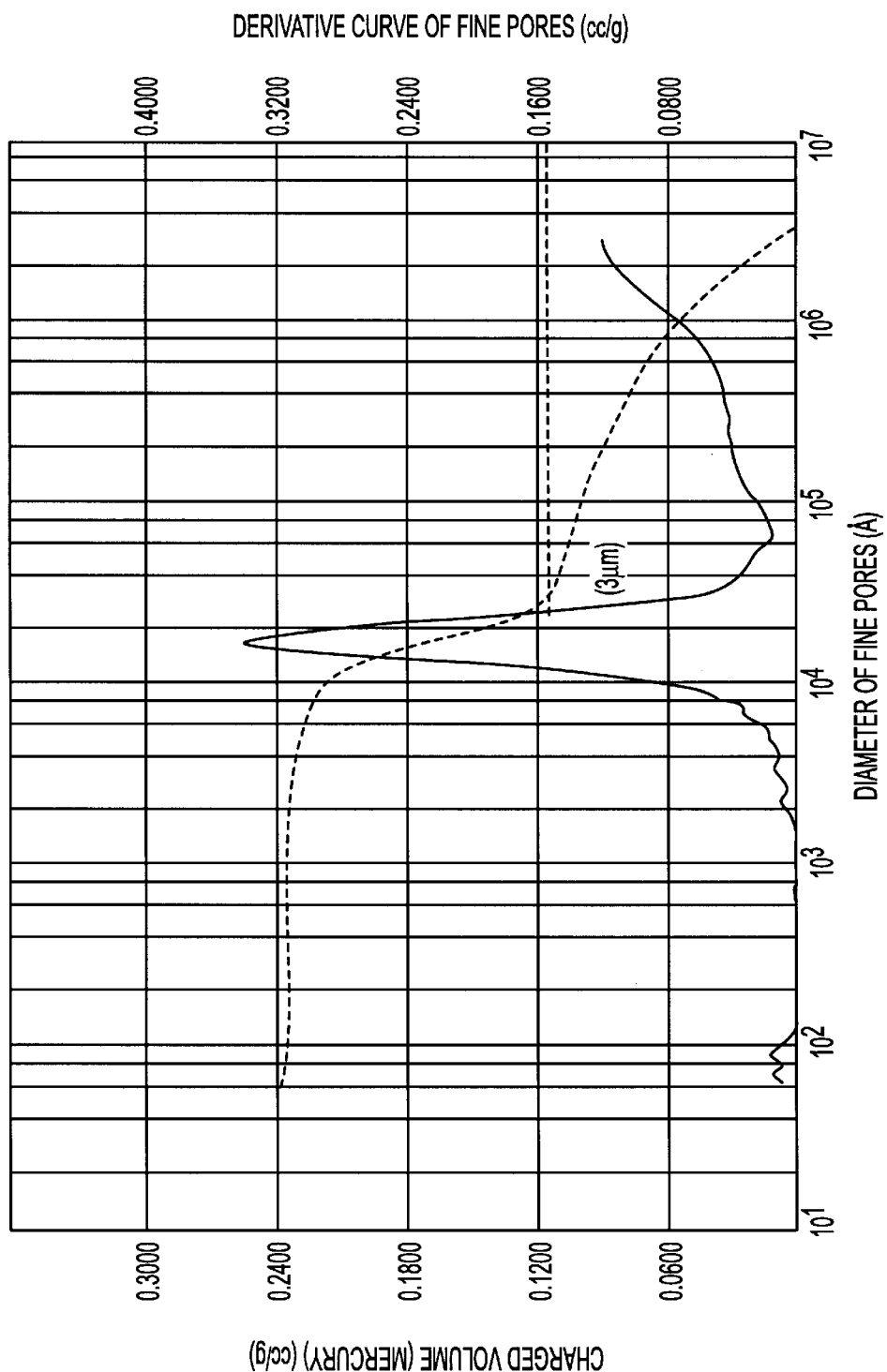
FIG. 13 is a graph showing a dispersion of fine pores in the prior art body (a specimen of FIG. 7 as plotted by a press charged mercury method)
Figure 14:
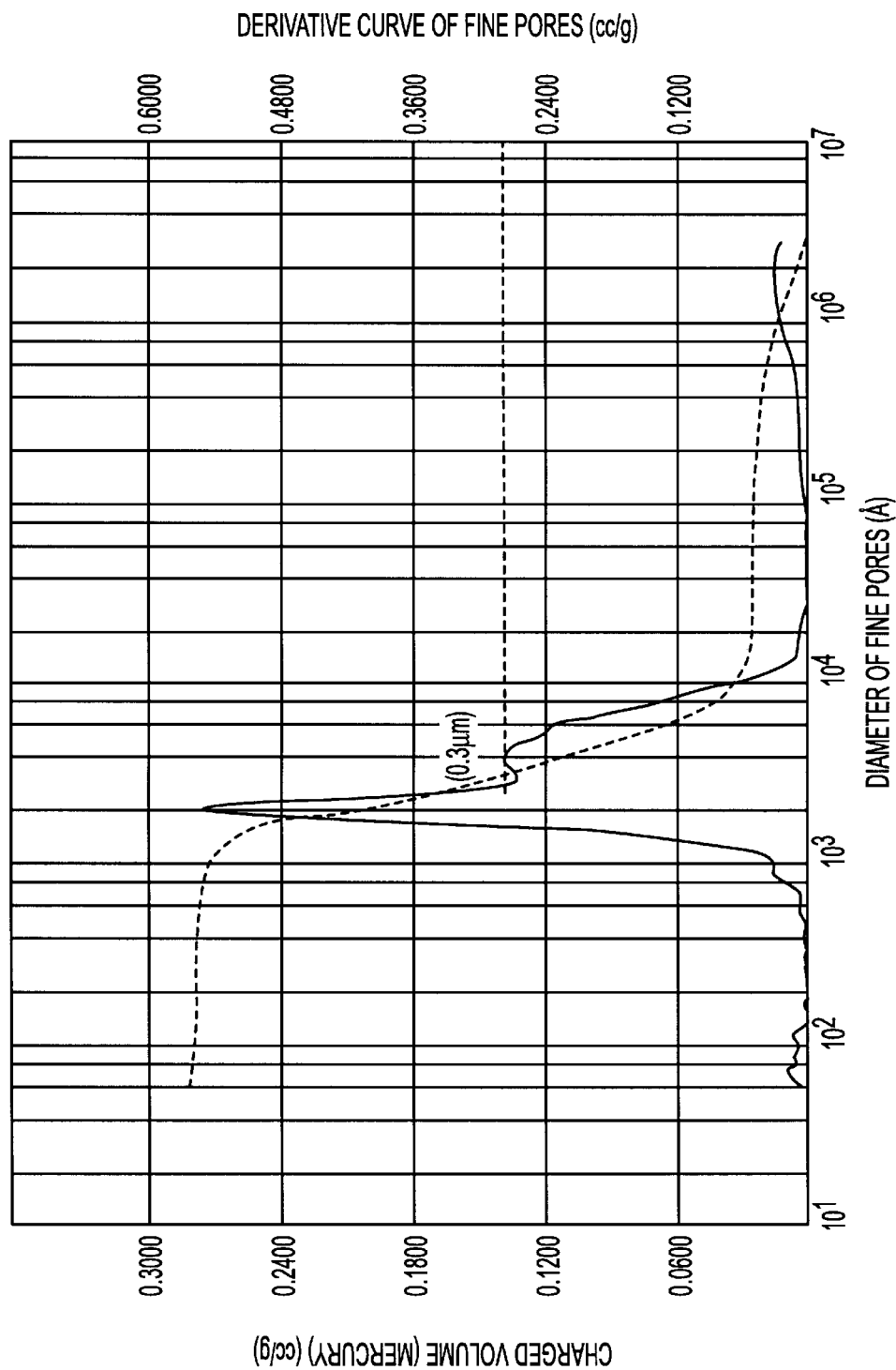
FIG. 14 is a graph showing a dispersion of fine pores in the prior art body (a specimen of FIG. 8 as plotted by a press charged mercury method)
Figure 15:
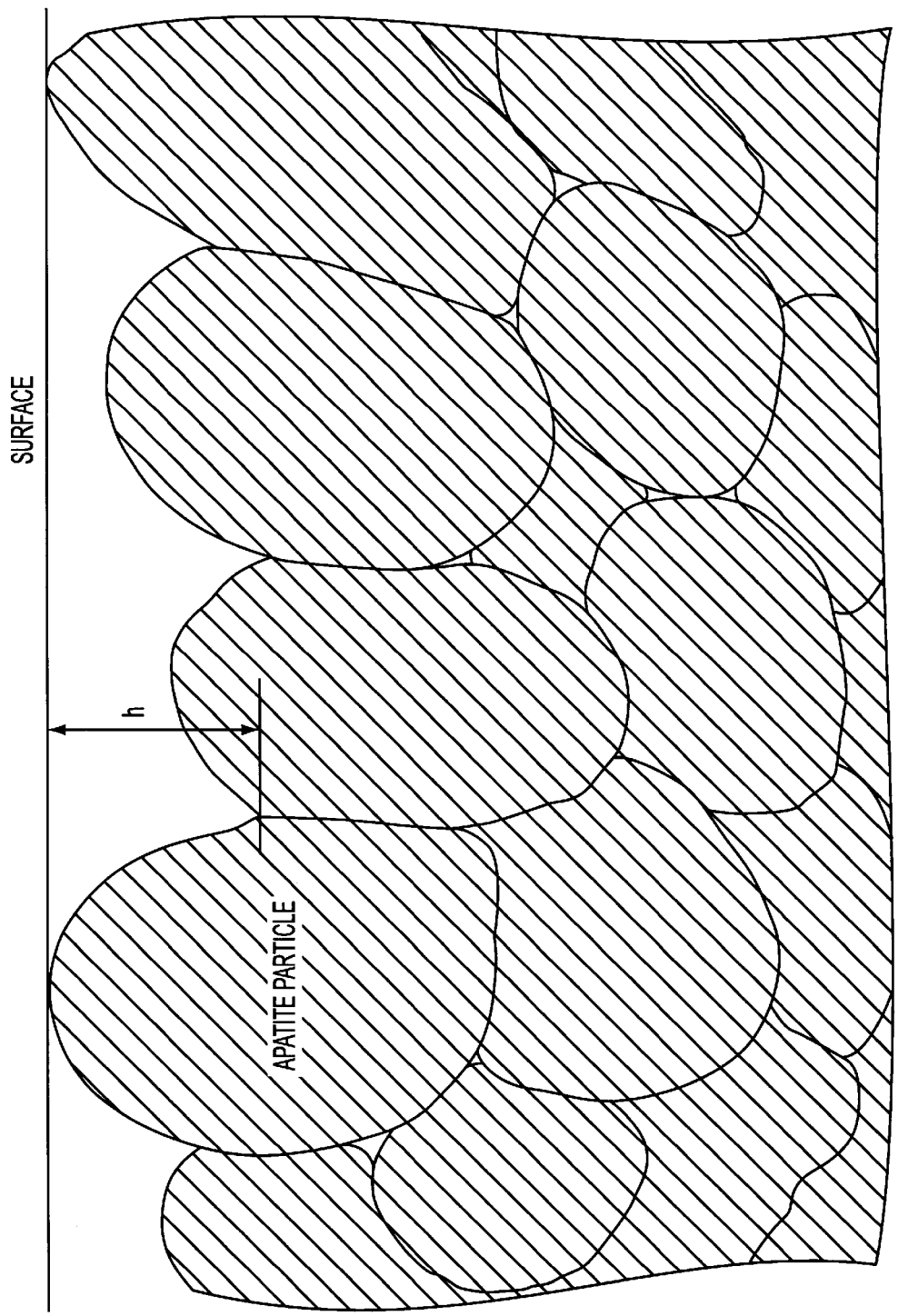
FIG. 15 is an explanatory view of the recesses formed between the particles on the wall surface which forms a pore.

Here, FIG. 9 is a distribution map of fine pores plotted on the basis of the mercury porosimeter examination for the porous ceramics body for in vivo use according to the present invention (a specimen shown in FIG. 3); FIG. 10 is a distribution map of fine pores plotted on the basis of mercury prosimeter examination for the prior art counterpart (the specimen shown in FIG. 4); and FIG. 11 is a distribution map of fine pores plotted on the basis of mercury prosimeter examination for the prior art counterpart (the specimen shown in FIG. 5); FIG. 12 is a distribution map of fine pores plotted on the basis of mercury prosimeter examination for the prior art counterpart (the specimen shown in FIG. 6); FIG. 13 is a distribution map of fine pores plotted on the basis of mercury porosimeter examination for the prior art counterpart (the specimen shown in FIG. 7); and FIG. 14 is a distribution map of fine pores plotted on the basis of mercury porosimeter examination for the prior art counterpart (the specimen shown in FIG. 8).

In this connection, the solid line in each figure is representative of the distribution of the diameter of fine pores whereas the dotted line therein is representative of the distribution of the total volume thereof.

As shown FIG. 9, the porous ceramics body according to the present invention has a distribution of fine pores (measured by the mercury porisimeter examination) showing that the pores account for 80% or more of all the pores in terms of volumes have a diameter of 5 micron (5 $\mu$m) or more and it is preferable that so do the pores accounting for 90% or more.

Therefore, the volume of the pores each having a diameter of 5 micron (5 $\mu$m) or less accounts for less than 20% of the total volume of all the pores therewithin and it is preferable that so do the pores accounting for less than 10%.

In the prior art, on the other hand, FIGS. 10 through 14 show that the volume of the pores each having a diameter of 5 $\mu$m or more accounts for 50% or less while pores accounting for at least 50% or more thereof have fine pores (each having a diameter of less than 5 $\mu$m).

In this connection, the fine pore distribution (distribution plotted on the basis of the result of measurement by the mercury porosimeter examination) shown in FIG. 9 indicates that the diameters of the pores accounting for an accumulated percentage of 50% are about 60 $\mu$m. Further, the fine pore distribution (plotted on the basis of the result of measurement by the mercury porosimeter examination) as shown in FIGS. 10 through 14 indicates that the diameters of the pores accounting for an accumulated percentage of 50 are about 0.1 $\mu$m (FIG. 10), about 2.5 $\mu$m (FIG. 11), about 1.5 $\mu$m (FIG. 12), about 3 $\mu$m (FIG. 13), and about 0.3 $\mu$m (FIG. 14).

From the above data, it is noted that the porous ceramics body according to the present invention has a very small number of or substantially no fine pores in the wall portions.

In this way, since the porous ceramics body according to the present invention is made of a sintered porous ceramics material having a very small number of pores in the wall portion of the porous body, said porous body is excellent in strength property such as bending strength. If the bending strength is lower to the level of the prior art, it is possible to have a higher percentage of pores.

The porous ceramics body for in vivo use (that is, the porous ceramics body made of a sintered hydroxy apatite having the pore percentage of 75%, the pore diameter (central value) of spherical pores of 150 $\mu$m) has a bending strength of 5 to 8 MPa which is two to three times a similar prior art sintered body (the pore percentage of 70% or thereabout and the average pore diameter of 200 $\mu$m).

Now, according to the present invention, it is preferable that calcium phosphate particles formed through granular growth by sintering constitute the body. In this case, a plurality of material particles fuse each other until particles rounded overall are observed on the surface by microscope. The surface of the porous ceramics body are relatively smoothly constructed by closely spreading said calcium phosphate particles overall such that the irregularities formed in the form of recesses between a given calcium phosphate particle on the surface and another given adjoining calcium phosphate particle on the surface are equal to or less than the mean particle diameter, thus ensuring that the body fluid is kept from stagnating to make it easy for the human cells to stick thereto uniformly and overall.

Further, the particles hardly fall off from the surface of the wall portions of the porous ceramics body such that there is no cause for cracks to be formed, thus improving the strength thereof.

Further, since the surface of the wall portions spread with the calcium phosphate particles are in the shape of a reversed figure of the letterwin cross section, it is assumed that cells are effectively nested in tiny recesses defined therebetween. Further, calcium phosphate particles are securely joined to each other to prevent them from falling off therefrom such that washing thereof is easily done.

Further, the handling thereof at the time of a surgical operation is so easy that powder is hardly produced by any partial breakage. It is also possible to provide a shape to fit that of broken part of the patient's bone. Further, if the broken part of the patient's bone is to be refilled with the porous ceramics body in the form of granules which will not be squashed under refilling work, the porous structure of the refilling material is maintained to assure effective formation of osseous issues.

Further, it is preferable in the porous ceramics body according to the present invention that the diameter of the communication ports 3 in the form of a series of spherical pores is in the range of 10 to 600 μm (central value) for the accumulated volume percentage of 50% by press charged mercury method.

In this way, the structure of the porous ceramics body is aimed at easy entry of osseous tissues (osteoblast cells) or capillary vessels thereinto for stable and effective osseous formation. Thus, the entry of osseous cells (osteoblast cells) is not easy with a pore diameter of less than 10 μm (central value) while the circulation of the body fluid increases to such an extent that the cells will not take root due to flowout thereof at more than 600 μm.

Further, the pore percentage of the porous ceramics body for in vivo use in accordance with the present invention is in the range of 45% to 90%.

If the porosity ratio is less than 45%, the osseous tissue cells (osteblast cells) or blood vessels will not enter the porous ceramics body easily. On the other hand, it is impossible to maintain a sufficient strength with the porosity ratio of more than 90%. It is preferable in the present invention that the porosity ratio is in the neighborhood of 75%.

Further, the porous ceramics body according to the present invention is preferably provided with fine irregularities in the wall portions 1 within the pores of said porous ceramics body and said irregularities are defined by sintered material particles such that the osseous system cells (osteblast cells) take root to facilitate the osseous formation.

Specific examples of sintered calcium phosphates which constitute the porous ceramics include tricalcium phosphate, hydroxy apatite, oxy apatite, quatrocalcium phosphate and combinations thereof. Of said materials, hydroxy apatite, tricalcium phosphate and the combinations thereof are particularly preferable.

Next, a method of manufacturing sintered calcium phosphates constituting porous ceramics body according to the present invention will be explained taking hydroxy apatite as an example.

For example, a cross linked polymeric resin such as polyethylene imine [Mn: about 8000~10500] is added to hydroxy apatite $[Ca_{10}(PO_4)_6(OH)_2]$ in powder form having a mean diameter of 0.1 to 5 μm together with ultra pure water as a dispersion medium therefor to mix and pulverize into a slurry.

Next, a foaming agent (a member selected from polyoxy ethylene laurylether, lauryl betaine, and lauryl triethanol sulfate amine) is added to stir and foam the mixture.

Further, a cross linking agent (sorbitol polyglycin diether or the like) is added thereto before the foamed slurry is poured into mold where the foamed slurry is fixed and dried to be further subjected to sinter the same at a temperature of 1100° C. to 1300° C. to obtain a sintered porous hydroxy apatite body.

This sintering step is done for 0.5 to 3 hours and the resultant body is known as a completely sintered porous body.

It is to be noted here that the complete sintering indicates a state in which crystalline particles forming a sintered body are sufficiently connected each other leaving no gaps therebetween such that there are no pores substantially smaller than the crystalline particles all over the sintered body.

Therefore, the fine pores in the wall portions 1 of the body of the porous ceramics body disappear while the wall portions 1 of the body are formed with fine irregularities on the surfaces thereof.

In the method according to the present invention, since the pores are closely arranged within the tissues, the wall portions of the porous ceramics body which partition the respective adjoining pores are so thin as to collapse on drying or sintering to define communication ports. Further, since no press molding is involved in the manufacture of the porous ceramics body, a sintered body having a high porosity is easily obtained.

Further, since the porous body is completely sintered, fine pores are prevented from being formed in the wall portions.

Since the thus obtained porous ceramics body for in vivo and in vitro use according to the present invention is excellent in prompting the in vivo osseous formation while maintaining the mechanical strength, it makes a suitable artificial bone or an artificial osseous filling material. Particularly, a sintered hydroxy apatite body is most suitable for artificial bones or artificial filling materials.

EXAMPLES

Example 1

A slurry was prepared by adding, as a cross linked polymeric resin, 10.5 parts by weight of polyethylene imine (Mn8000 to 10500) to 100 parts by weight of powdered hydroxy apatite $[Ca_{10}(PO_4)_6(OH)_2]$ having a mean diameter of 0.3 μm together with 70 parts by weight of ultra pure water as a dispersion agent for mixing and pulverizing.

Next, 0.3 parts by weight of a foaming agent (polyoxyethylene laurylether) was added to said slurry to be stirred and foamed.

Further, 3.5 parts by weight of cross linking agent (sorbitol polyglycin diether or the like) was added to fix the foam structure before the foamed slurry is poured into a mold to be dried and then, sintered at a temperature of 1200° C. for one hour to obtain a specimen (100×100×100 mm) of a sintered hydroxy apatite body (porous ceramics body for in vivo use).

Said specimen was subjected to mercury porosimeter examination to measure the distribution of the pores and the result is shown in FIG. 9.

It was disclosed from FIG. 9 that pores having diameters of 5 μm or more accounts for 97% or more of the entire pores in the thus obtained porous ceramics body for in vivo use whereas fine pores having a diameter of less than 5 μm scarcely exist. Further, the porosity calculated from the bulk specific gravity and the true specific gravity is 75%. Further, the bending strength measurement of the porous ceramics body specimen is 8 MPa.

Comparative Example 1

Three types of commercially available calcium phosphates [including (A) the specimen shown in FIG. 4 (manufactured by company A): HAp (hydroxy apatite) having a porosity of 70%; (B) the specimen shown in FIG. 5 (manufactured by company B) HAp of 70%, β-TCP (tricalcium phosphate) of 30%, a porosity of 55%; (C) the specimen shown in FIG. 6 (manufactured by company C)β-TCP, a porosity of 75%) were prepared and subjected to the examination in accordance with the press charged mercury method to show obtained results in FIGS. 10 through 12.

From the figures, it was observed that the prior art sintered porous body had a considerably larger number of fine pores having a diameter of less than 5 μm than the embodiments.

Now, the bending strength in A was 2 MPa; that in B was 4 MPa; and that in C was 3 MPa.

Reference Example

A tiny piece having a diameter of 10 mm and a length of 4 mm was prepared from the specimen used in Embodiment 1. Said piece was subjected to a normal sterilization process and, thereafter, was implanted in the back of a rat.

As a result, it was observed two weeks later that cells entered the porous body a week earlier than the commercially available product A.

In this connection, although it was explained that the porous body suits an artificial bone or an artificial osseous filling material in the above embodiment, the porous ceramics body for in vivo or in vitro use according to the present invention can be suitably used for a material used for controlled release of chemicals within a living body. Particularly, tricalcium phosphate is suitable as the material for controlled release of chemicals as porous ceramics body for in vivo use.

Since the porous ceramics body for in vivo or in vitro use according to the present invention is made of a sintered calcium body having a particular structure, in vivo osseous formation is promptly done and excellent in the strength, thus providing a suitable material as artificial bones, artificial osseous filler, a material for controlled release of chemicals or a culture vessel for cells.

What is claimed is:

1. A porous ceramics body for in vivo or in vitro use in which a number of pores are closely distributed in three dimensional directions, adjoining pores thereof being partitioned by wall portions which are formed with respective communication ports to bring said adjoining pores into communication with each other such that a series of spherical pores are formed therewithin, wherein each wall portion has a surface spread with calcium phosphate particles such that adjoining calcium phosphate particles cooperate to define a recess therebetween, said recess having a depth equal to or less than a mean particle diameter;

said porous ceramics body being made of a sintered calcium phosphate body that has a porosity of 45 to 90%, wherein said sintered calcium phosphate body open pores each having a diameter of 5 microns ($\mu$m) or more account for 80% or more of all the pores in terms of volume whereas open pores having a diameter of less than 5 microns ($\mu$m) account for less than 20% of all the pores in terms of volume as subjected to a mercury porosimeter measurement.

2. A porous ceramics body for in vivo or in vitro use in which a number of pores are closely distributed in three dimensional directions, adjoining pores thereof being partitioned by wall portions which are formed with respective communication ports to bring said adjoining pores into communication with each other such that a series of spherical pores are formed therewithin, said porous ceramics body being made of a sintered calcium phosphate body that has a porosity of 45 to 90%, wherein said sintered calcium phosphate body pores accounting for an accumulated ratio of 50% in terms of volume have a diameter of 10 to 100 microns ($\mu$m) as subjected to a mercury porosimeter measurement.

3. A porous ceramics body for in vivo or in vitro use as set forth in claim 1, wherein said sintered calcium phosphate body is a sintered body made of a material selected from the group consisting of hydroxy apatite, tricalcium phosphate and a composite material thereof.

4. A porous ceramics body for in vivo or in vitro use as set forth in claim 3, wherein each wall portion has a surface spread with calcium phosphate particles, given adjoining calcium phosphate particles cooperating to define a recess therebetween, said recess having a depth equal to or less than a mean particle diameter.

5. A porous ceramics body for in vivo or in vitro use as set forth in claim 2, wherein said sintered calcium phosphate body is a sintered body made of a material selected from the group consisting of hydroxy apatite, tricalcium phosphate and a composite material thereof.

6. A porous ceramics body for in vivo use as set forth in claim 2, wherein each wall portion has a surface spread with calcium phosphate particles, given adjoining calcium phosphate particles cooperating to define a recess therebetween, said recess having a depth equal to or less than a mean particle diameter.

7. A porous ceramics body for in vivo or in vitro use as set forth in claim 5, wherein each wall portion has a surface spread with calcium phosphate particles, given calcium phosphate particles cooperating to define a recess therebetween, said recess having a depth equal to or less than a mean particle diameter.

* * * * *